United States Patent [19]

Lau et al.

[11] 3,998,642
[45] Dec. 21, 1976

[54] SILVER HALIDE EMULSIONS WITH INCORPORATED 4,6-DIFLUOROPHENOLIC COUPLERS

[75] Inventors: Philip T. S. Lau; Roy L. Orvis, both of Rochester; Thomas E. Gompf, Penfield, all of N.Y.

[73] Assignee: Eastman Kodak Company, Rochester, N.Y.

[22] Filed: July 11, 1975

[21] Appl. No.: 594,988

[52] U.S. Cl. .................. 96/100; 96/55; 260/612 R
[51] Int. Cl.² .................. G03C 1/40
[58] Field of Search .................. 96/100, 55

[56] References Cited

UNITED STATES PATENTS

| | | |
|---|---|---|
| 2,367,531 | 1/1945 | Salminen et al. .................. 96/100 |
| 2,423,730 | 7/1947 | Salminen et al. .................. 96/100 |
| 3,516,831 | 6/1970 | Wolf et al. .................. 96/100 |
| 3,647,452 | 3/1972 | Hendess et al. .................. 96/100 |
| 3,758,308 | 9/1973 | Beavers et al. .................. 96/100 |
| 3,790,384 | 2/1974 | Oishi et al. .................. 96/100 |
| 3,926,634 | 12/1975 | Sugizaki et al. .................. 96/100 |

*Primary Examiner*—J. Travis Brown
*Attorney, Agent, or Firm*—J. G. Levitt

[57] ABSTRACT

Color photographic elements are disclosed having, incorporated therein, one or more novel phenolic materials which have the following structure:

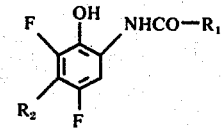

wherein $R_1$ is a non-interfering alkyl, aryl, amino, substituted alkyl or substituted aryl ballasting group of the type which is useful in photographic incorporated cyan color-forming couplers, and $R_2$ is hydrogen or a lower alkyl group.

7 Claims, No Drawings

SILVER HALIDE EMULSIONS WITH INCORPORATED 4,6-DIFLUOROPHENOLIC COUPLERS

This invention relates to photosensitive materials. More particularly, this invention relates to color photographic elements containing incorporated color-forming couplers.

BACKGROUND

The formation of colored photographic images by the coupling of oxidized aromatic primary amino developing agents with color-forming or coupling compounds is well known. In these processes the subtractive process of color formation is ordinarily used and the image dyes are intended to be cyan, magenta, and yellow, the colors that are complementary to the primary colors. Usually phenol or naphthol couplers are used to form the cyan dye image, pyrazolone or 2-(alpha-cyanoacetyl)-coumarone couplers are used to form the magenta dye image, and open-chain reactive methylene couplers having two carbonyl groups attached to the active methylene group (which is often substituted with a so-called "coupling off" group such as halogen, aryloxy, thioheterocyclic, and the like) are used to form the yellow dye image.

In these color developing processes the color forming coupler may be either in the developer solution or incorporated in the light-sensitive photographic emulsion layer so that during development it is available in the emulsion layer to react with the color developing agent that is oxidized by silver image development. Diffusible type couplers are used in color developer solutions. So-called Fischer type couplers and nondiffusing couplers which are soluble in high boiling solvents are incorporated in photographic emulsion layers. When the dye image formed is to be used in situ, couplers are selected which form nondiffusing dyes.

Conventional color-forming couplers are often four-equivalent, that is, they require the development of four molecules of silver halide in order to form one molecule of dye. Two equivalent couplers require the development of only two molecules of silver halide to bring about the formation of one molecule of dye. Two-equivalent couplers are very desirable for color photography, since only about one-half the usual amount of silver halide is needed and the light-sensitive coatings can thus be made thinner. Certain of the available two-equivalent couplers form dyes upon reaction with oxidized color developing agent, which dyes are subject to a gradual loss of color intensity, called "fading" when they are exposed to light and/or heat for a prolonged period of time. The fading of a colored photographic image is undesirable and much effort has been expended to date in efforts to minimize image fading.

THE PRESENT INVENTION

It has now been found that image dye in the "cyan" layer of color photographic elements can be made extremely resistant to "heat fade" by using in that layer an incorporated coupler having the following structure:

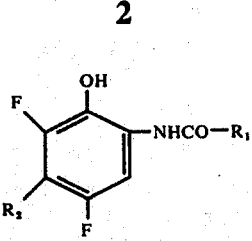

wherein $R_1$ is a ballasting group of the type used in incorporated cyan color-forming couplers and $R_2$ is either hydrogen or a lower alkyl group of 1-6 carbon atoms. It has been observed that unless both fluorine atoms are present in the coupler molecule, and in the 4,6-position on the phenolic ring, the excellent resistance to heat fading displayed by the 4,6-difluoro-2-amidophenol-containing compositions of this invention cannot be obtained.

THE PRIOR ART

Phenolic couplers are well known in the art. In U.S. Pat. No. 2,367,531, couplers are described having the structure:

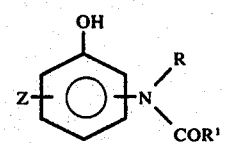

with "Z" being described as follows:

Other substituents (Z) may or may not be present in the aminophenol nucleus, for example, alkyl, aryl or halogen.

No preference for substituents at the 4,6-positions are described in this patent. The only halogen specifically set out by these patentees is chlorine.

In U.S. Pat. No. 2,423,730, phenolic couplers are described having the structure:

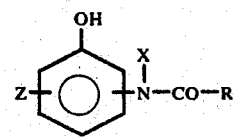

with "Z" being generically described as:

. . . hydrogen or one or more substituents such as halogen or hydrocarbon. The halogen substituents include chlorine, bromine and iodine . . .

Fluorine is absent from the description of the "halogen" substituents taught by these patentees, and from the many specific examples set out in this patent. No preference is suggested in this patent for substituents on the phenolic ring at the 4 and 6 positions.

In U.S. Pat. No. 3,647,452, phenolic couplers having the structure:

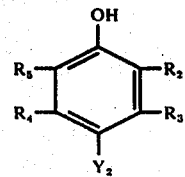

wherein $R_2$, $R_3$, $R_4$, $R_5$ and $Y_2$ are described as being ". . . a halogen (e.g, chlorine, bromine, fluorine). . ." among many other types of substituents. No preference is shown for any of these substituents at the 4 and 6 positions by these patentees. Also, this patent is directed to competing couplers which are soluble in color developer solutions, as compared with the incorporated couplers of the present invention.

DETAILS RELATING TO THE INVENTION

The present invention comprises light sensitive photographic silver halide emulsions which contain, in addition to the silver halide at least one hydrophilic colloid such as gelatin, for example, and at least one phenolic color-forming coupler compound having the structure:

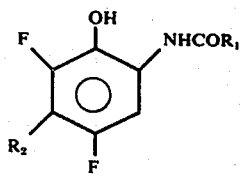

wherein
 $R_1$ is a ballasting group of the type used in photographic incorporated cyan color-forming phenolic couplers and
 $R_2$ is lower alkyl of 1 to about 5 carbon atoms or hydrogen.

The —$NHCOR_1$ group represents herein any acylamino group which has been found useful in phenolic coupler compounds, which does not prevent the desired color-forming coupler activity of the resulting compound and which can serve in the well-known manner as a ballasting group. Thus, the particular identity of this acylamino group is not critical insofar as the successful practice of this invention is concerned, so long as the group functions effectively as a ballasting group to prevent the phenolic coupler compound from migrating or diffusing through the hydrophilic colloid layer in which the coupler is dispersed. Typical, nonlimiting examples of useful acylamino ballasting groups can be found in U.S. Pat. Nos. 2,367,531; 2,166,181; 2,772,162; 2,242,337; 2,369,929; 2,423,730; and 3,446,622; and U.K. Pat. No. 576,963; French Pat. No. 1,308,760 and German Pat. No. 1,163,144, and include those in which $R_1$ is substituted alkyl, aryl, substituted aryl, heterocyclic, alkylphenoxyphenyl, phenoxyalkyl, 2-ethoxyphenyl, 2-(2,4-di-tertamyl)phenoxyacetamido, alkyl thiazolyl, alkylbenzothiazolyl, naphtholthiazolyl, alkylbenzothiazolyl, benzoxazolyl, benzimidazolyl, ureido, such as —$NHC_{14}H_{29}$ or —$NHCOC_{15}H_{31}$ and the like.

$R_2$ is preferably methyl.

The ballasted 4,6-difluorophenolic couplers of the present invention are of the nondiffusing type and are used to advantage in photographic emulsion layers. These couplers can be incorporated into a photographic emulsion layer by any of the techniques set out in U.S. Pat. Nos. 2,304,939 or 2,322,027 whereby the coupler is dissolved in high-boiling solvents. The resulting solutions are then dispersed through the emulsion by any of the methods described in U.S. Pat. Nos. 2,801,701; 2,801,171; or 2,949,360.

The present couplers are useful in the color development of photographic hydrophilic colloid-silver halide emulsion layers, including photographic elements containing such layer(s). In photographic elements used for the reproduction of color objects or scenes, generally the present couplers will be associated with (and preferably incorporated into) the one or more photosensitive layers in the elements, which layers have been specially sensitized to the red region of the visible spectrum. The present photosensitive photographic emulsions may contain silver chloride, silver bromide, silver iodide, silver chlorobromide, silver bromoiodide, silver behenate, cuprous chloride, a cobalt hexammine complex salt, and the like as the light-sensitive material.

Any hydrophilic colloid useful in the manufacture of a photographic element can be used in the successful practice of this inventon. For example, those set out at column 8, lines 43–68 of U.S. Pat. No. 3,644,498 can be used, as can those referred to in the paragraph entitled "VIII. VEHICLES" on page 108 of *Product Licensing Index*, Vol. 92, December, 1971, publication 9232.

Typically, the emulsions that are used in the manufacture of the present photographic elements can be chemically and spectrally sensitized in any conventional manner, including those referred to in Sections III and XV, pages 107 and 108, respectively in *Product Licensing Index*, Vol. 92, December, 1971. Such emulsions can also contain any desired useful addenda such as antifoggants, stabilizers, speed modifiers, antistatic materials, filter dyes, matting agents, brighteners, coating aids, ultraviolet absorbers, hardeners, and the like. Usage of such addenda is detailed in many of the references set out in paragraphs IV, V, VII, IX, XII, XIII, XIV and XVI of the aforementioned Product Licensing Index article, pages 107–109.

Methods and compositions for both manufacturing and processing photographic elements containing incorporated couplers such as those of the present invention are well known. Techniques for coating (and drying) layers of photographic emulsions like those of the present invention can be found in the references cited in part XVIII "Coating Procedures" of Product Licensing Index, Vol. 92, December 1971, page 109. Processing details can be found in the reference set out in part XXIII "Processing" of that same article on page 110.

The emulsions of the present invention can be coated on a wide variety of photographic emulsion supports. Typical supports include cellulose nitrate film, cellulose acetate film, polyvinyl acetal film, polystyrene film, polyethylene terephthalate film, polyethylene film, polypropylene film, and related films of resinous materials, as well as paper, glass and others.

Usually the emulsions of this invention are coated on photographic supports in the form of multilayer color photographic elements wherein at least three differently sensitized emulsion layers are coated over one another on the support. Usually the support is coated in succession with one or more red-sensitive layers, one or more green-sensitive layers and one or more blue-sensitive layers either with or without yellow filter layer between the blue-sensitive and green-sensitive layers or units. The three differentially color sensitized layer units may be arranged in any other order over one another that is desirable; however, the Carey Lea filter layer obviously would not be put over the blue-sensitive layer. Preferably, these light-sensitive layers are arranged on the same side of the support. Also, hydrophilic colloid layers which can also contain other addenda can be present between these emulsion layers, on either side of the support (or both sides), and as an overcoat layer.

Elements made for image transfer processing may use a separate receiving sheet which is contacted with the light-sensitive layer during its development, or the receiving layer may be an integral part of the light-sensitive element.

EXAMPLES

Several photographic elements were coated conventionally with single layers of gelatinous silver halide emulsions on a conventional transparent photographic cellulose acetate support. The coatings contained (per square decimeter) the following materials: 14.69 mg silver, 48.60 mg. gelatin 8.21 mg. coupler (couplers identified below), and 4.21 mg di-n-butylphthalate coupler solvent. Each of the samples were sensitometrically exposed through a graduated density test object and conventionally color processed at 20° C. The color process included color development, stop-fix, wash, bleach, wash, fix, wash, stabilize and dry steps, each in a conventional manner.

In the following tables, "developer solutions" A and B were made up as follows:

| Solution A | |
|---|---|
| Water | 800 ml |
| Sodium hexametaphosphate | 0.5 g. |
| $Na_2SO_3$ | 2.0 g. |
| 4-amino-3-methyl-N,N-diethyl aniline hydrochloride | 2.0 g. |
| $Na_2CO_3 \cdot H_2O$ | 20.0 g. |
| 50% by weight NaBr Solution | 3.46 ml |
| Water to make 1 liter total (pH = 10.86) | |
| Solution B | |
| Water | 800 ml |
| Benzyl alcohol | 4.0 ml. |
| Sodium hexametaphosphate | 0.5 g. |
| $Na_2SO_3$ | 0.4 ml. |
| 4-Amino-3-methyl-N-ethyl-N-Beta-(methylsulfonamide)-ethyl-aniline sesquisulfate hydrate | 5.0 g. |
| 50% by weight NaBr solution | 1.72 ml |
| Water to 1 liter (pH=10.75) | |

Data for "Heat Fade" in the following tables resulted from subjecting each of the samples, after the processing sequence, to a temperature of 77° C. at a relative humidity of >5% for 1 and 2 weeks. Dye density was then recorded in an area of the sample which had an initial dye density of about 1.2. In the following tables, "Heat Fade" data are presented in terms of percent fading as a result of storage in a dark, hot, dry environment, lower figures being better than higher figures. "Control" couplers in each Test Set, below, are either conventional couplers or other compounds which are structurally similar to the couplers of this invention which were tested, with the exception of the halogen substituents on the phenolic ring.

Test Set 1

| Coupler | Developer Solution | Dmax | λmax | Heat Fade(%) 1 week | 2 week |
|---|---|---|---|---|---|
| Control 1* | A | 3.82 | 671 | 58 | 70 |
| | B | 3.80 | 648 | 18 | 37 |
| Control 2** | A | 3.30 | 678 | 9 | 18 |
| | B | 3.17 | 651 | 3 | 8 |
| Invention 1*** | A | 2.40 | 643 | 3 | 1 |
| | B | 1.99 | 633 | 3 | 2 |

*Control Coupler No. 1

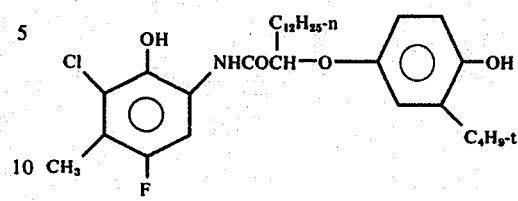

**Control Coupler No. 2

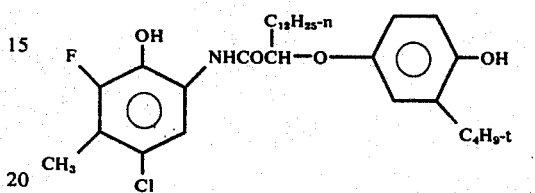

***Invention Coupler No. 1

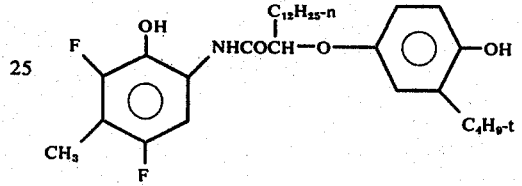

Test Set 2

| Coupler | Developer Solution | Dmax | λmax | % Heat Fade 1 wk. | 2 wks. |
|---|---|---|---|---|---|
| Control 3* | A | 3.47 | 655 | 12 | 23 |
| | B | 3.22 | 641 | 11 | 20 |
| Control 4** | A | 3.83 | 676 | — | 58 |
| | B | 3.85 | 668 | — | 42 |
| Invention 2*** | A | 3.32 | 673 | 9 | 18 |
| | B | 2.81 | 647 | 6 | 10 |

*Control Coupler No. 3

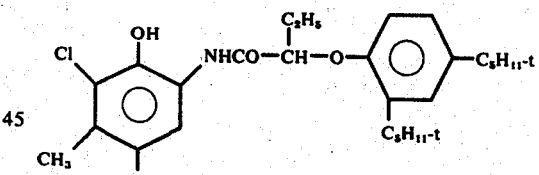

**Control Coupler No. 4

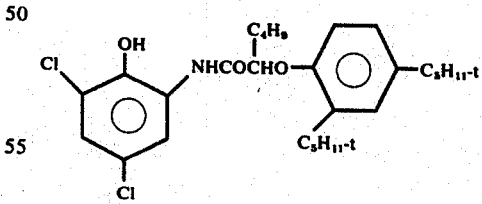

***Invention Coupler No. 2

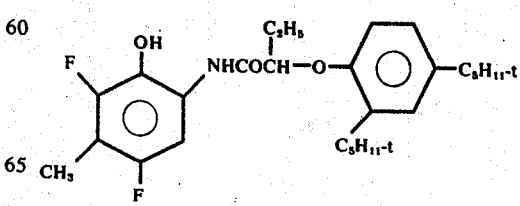

Test Set 3

-continued

| Coupler | Developer Solution | Dmax | λmax | % Heat Fade 1 wk. | 2 wks. |
|---|---|---|---|---|---|
| Control 5* | A | 3.47 | 655 | 12 | 23 |
|  | B | 3.22 | 641 | 11 | 20 |
| Invention 3** | A | 2.99 | 670 | 3 | 6 |
|  | B | 2.28 | 647 | 2 | 4 |

*Control Coupler No. 5

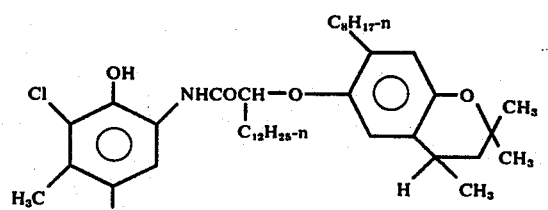

**Invention Coupler No. 3

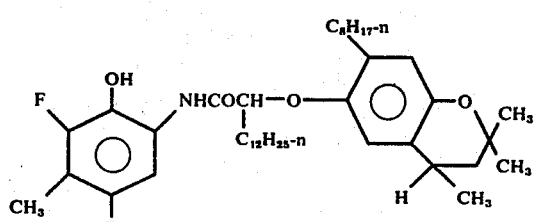

Test Set 4

| Coupler | Developer Solution | Dmax | λmax | % Heat Fade 1 wk. | 2 wks |
|---|---|---|---|---|---|
| Control 6* | A | 3.81 | 666 | 20 | — |
|  | B | 3.45 | 656 | 19 | — |
| Invention 4** | A | 2.16 | 658 | 2 | — |
| 01615. | B | 1.66 | 645 | 1 | — |

*Control Coupler No. 6

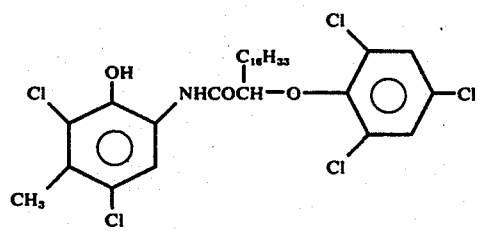

**Invention Coupler No. 4

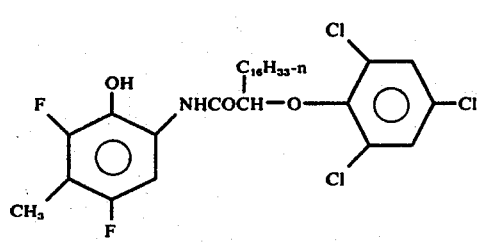

Test Set 5

| Coupler | Developer Solution | Dmax | λmax | % Heat Fade 1 wk. | 2 wks. |
|---|---|---|---|---|---|
| Control 7* | A | 2.53 | 661 | 12 | 26 |
|  | B | 2.74 | 648 | 12 | 27 |
| Invention 5** | A | 2.74 | 656 | 0 | 1 |
|  | B | 2.33 | 643 | 1 | 2 |

-continued

*Control Coupler No. 7

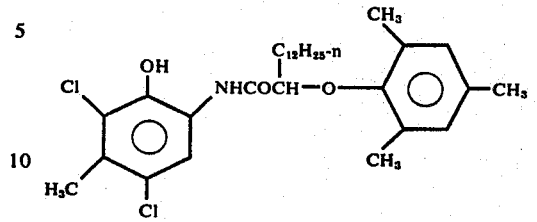

**Invention Coupler No. 5

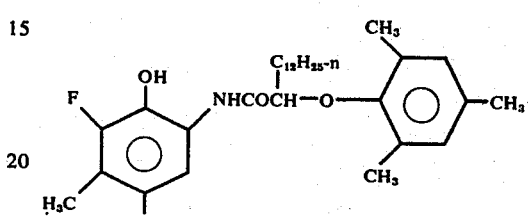

Test Set No. 6

| Coupler | Developer Solution | Dmax | λmax | % Heat Fade 1 wk. | 2 wks |
|---|---|---|---|---|---|
| Control 8* | A | 3.75 | 659 | 30 | — |
|  | B | 3.43 | 646 | 32 | — |
| Invention 6** | A | 1.95 | 654 | 0 | — |
|  | B | 1.45 | 641 | 2 | — |

*Control Coupler No. 8

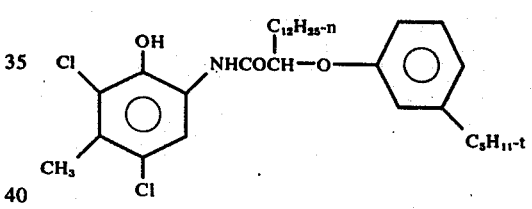

**Invention Coupler No. 6

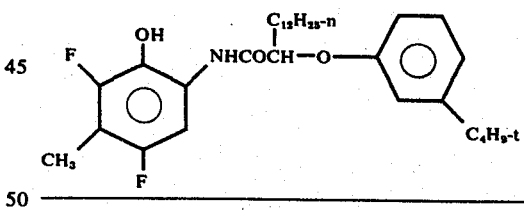

A study of the data from the foregoing "test sets" will readily reveal the surprisingly great resistance to "heat fading" that can be accomplished by practicing the present invention. Each of the foregoing "test sets" compared results using "invention" couplers which varied from their respective "control" couplers mainly in the type of halogen substituted at the 4 and/or 6 position on the phenolic ring.

In the following table, data is tabulated from tests in which substituents other than halogens were used at the 4-position on the phenolic ring, while Cl was used at the 6-position. Once again the great value of the present invention can readily be appreciated from such data, because of the extreme resistance to heat of the 4,6-difluoro-substituted materials.

Test Set No. 7
| Coupler | Developer Solution | Dmax | λmax | % Heat Fade 1 wk. | % Heat Fade 2 wks. |
|---|---|---|---|---|---|
| Control 9[a] | A | 3.68 | 690 | — | 26 |
|  | B | 3.47 | 683 | — | 16 |
| Control 10[b] | A | 3.78 | 688 | — | 30 |
|  | B | 3.72 | 681 | — | 14 |
| Control 11[c] | A | 1.59 | 663 | 14 | — |
|  | B | 1.66 | 655 | 5 | — |
| Invention 9[d] | A | 0.72* | 674 | 3 | 6 |
|  | B | 0.57* | 661 | 1 | 3 |
| Invention 10[e] | A | 3.12 | 648 | 5 | — |
|  | B | 2.78 | 639 | 0 | — |
| Invention 11[f] | A | 3.04 | 651 | 4 | — |
|  | B | 2.55 | 638 | 1 | — |
| Invention 12[g] | A | 2.04 | 666 | 5 | — |
|  | B | 2.42 | 650 | 5 | — |
| Invention 13[h] | A | 3.09 | 656 | 1 | — |
|  | B | 2.34 | 643 | 3 | — |
| Invention 14[i] | A | 0.96* | 661 | 4 | — |
|  | B | 0.79* | 648 | 2 | — |
| Invention 15[j] | A | 1.28 | 664 | 7 | — |
|  | B | 1.14 | 652 | 4 | — |
| Invention 16[k] | A | 1.55 | 656 | 2 | — |
|  | B | 1.64 | 630 | 2 | — |
| Invention 17[l] | A | 2.25 | 655 | 1 | — |
|  | B | 2.23 | 644 | 4 | — |
[a]Control Coupler 9
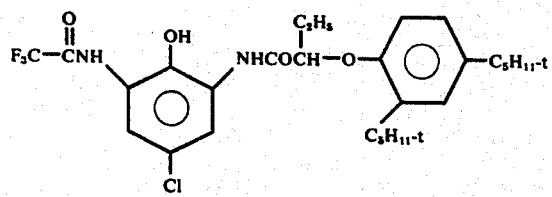
[b]Control Coupler 10
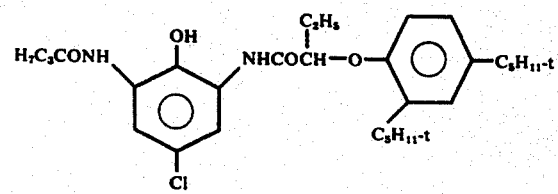
[c]Control Coupler 11
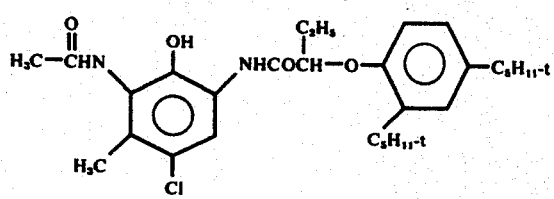
[d]Invention Coupler 9
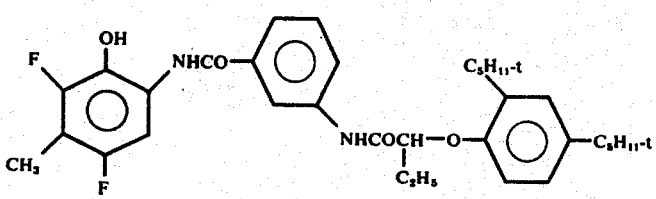
[e]Invention Coupler 10
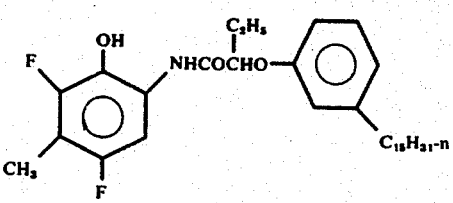

Test Set No. 7-continued
(*)Invention Coupler 11
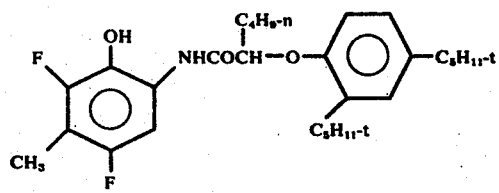
(*)Invention Coupler 12
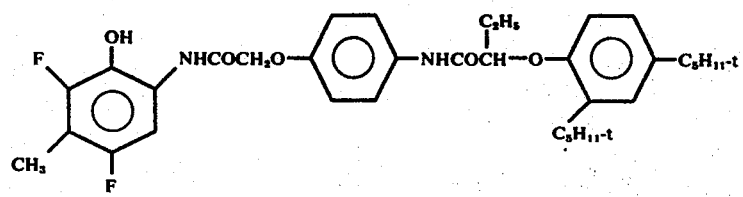
(*)Invention Coupler 13
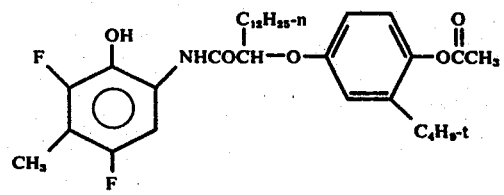
(*)Invention Coupler 14
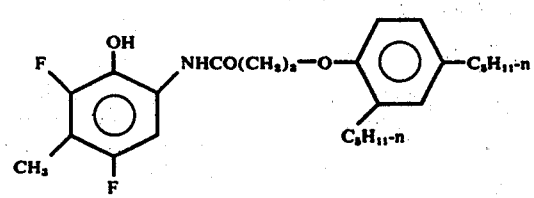
(*)Invention Coupler 15
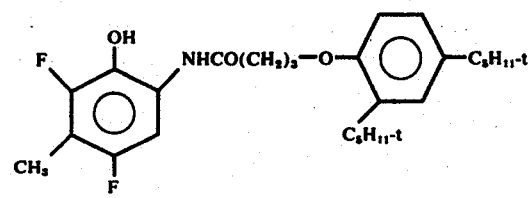
(*)Invention Coupler 16
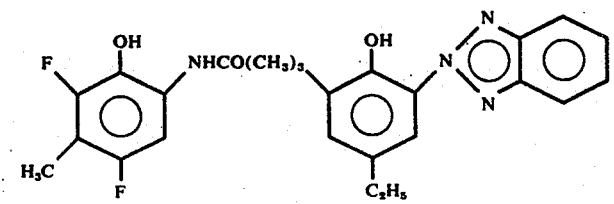

Test Set No. 7-continued

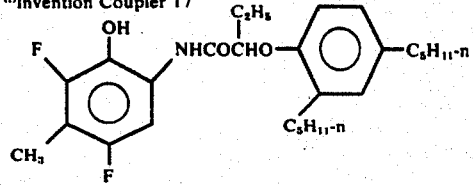

*Heat fade measured on densest portion.

SYNTHESIS OF COUPLERS OF THE INVENTION

A detailed process for manufacturing the 2,4-difluorophenolic couplers of the present invention is given below. Note that whereas the manufacture of only one of the couplers of this invention is described herein, appropriate raw materials and intermediates can be used in a known manner in the manufacture of any of the present coupler compounds.

Step 1

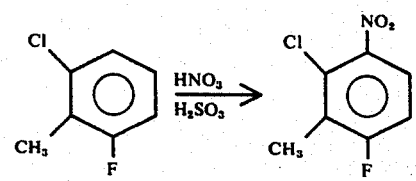

To a solution of 100 g (0.75 mole) of 2-chloro-6-fluorotoluene in 500 ml of glacial acetic acid and 500 ml of concentrated sulfuric acid at 0° C was added in 10 minutes a nitrating mixture of 150 ml of concentrated nitric acid and 100 ml of concentrated sulfuric acid. After one hour, a pale yellow solid precipitated and thin layer chromatography (TLC) (50% benzene — 50% cyclohexane on silica gel) showed that no starting material remained. The mixture was poured with stirring into an ice-water mixture and filtered 0° C. A yield of 116 g of crude, wet solid was obtained. Extraction of the filtrate with chloroform and evaporation of the chloroform extract yielded additional product. The total crude yield was 127 g (90%). The product was recrystallized from methanol, m.p. 39°–41° C.

Step 2

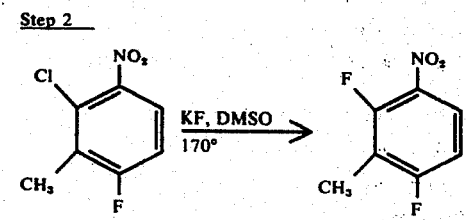

A solution of 120 g (0.63 mole) of 2-chloro-6-fluoro-3-nitrotoluene in 1 liter of anhydrous dimethyl sulfoxide was heated with stirring to 170° C. To this mixture was added 120 g. of anhydrous potassium fluoride in portions over a 30 minute period. The progress of the reaction was followed by TLC (50% benzene — 50% cyclohexane, silica gel). After 8 hours at 170° C, only a slight trace of starting material remained. The product was isolated by steam distillation from the reaction mixture. A total of 5 liters of distillate was collected, cooled and filtered. The crude weight of yellow solid was 100 g (90%). Recrystallization from methanol gave yellow crystals m.p. 38°–40° C.

Step 3

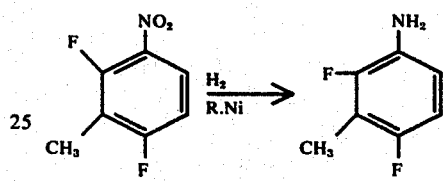

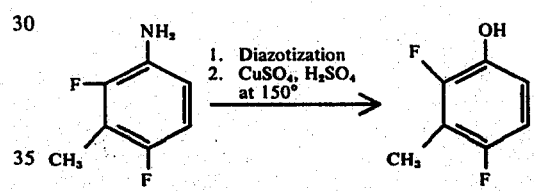

To a solution of 80 g (0.46 mole) 2,6-difluoro-3-nitrotoluene in 300 ml of absolute ethanol in a Parr hydrogenation bottle was added Raney nickel catalyst. The mixture was reduced at low pressure until there was no further uptake of hydrogen. The catalyst was filtered and the solvent evaporated to yield a heavy oil.

This amine was added dropwise at room temperature with vigorous stirring to a solution of 200 ml of water and 280 ml of concentrated sulfuric acid in a 1 liter, 3-necked flask fitted with a stirrer, condenser and addition funnel. A precipitate formed but quickly dissolved. The mixture was cooled to about 5° and a solution of 32.0 g (0.46 mole) of sodium nitrite in 30 ml of water was added dropwise with stirring below the liquid surface. Stirring at 0° C was continued for 30 minutes after all the sodium nitrite was added.

A solution of 400 g copper II sulfate in 300 ml of water and 1 liter of concentrated sulfuric acid in a 3-necked, 12 liter flask fitted with a steam inlet tube, condenser, thermometer and addition funnel was heated to 150° C. While steam was passed through the mixture, the diazonium solution was added dropwise into the flask. A total of 15 liters of distillate was collected, cooled and extracted with 5 liters of ethyl ether. The ether extract was dried over sodium sulfate and evaporated to yield a yellow oil. The product, which was purified by distillation at water pump pressure b.p. 91°–95° C, amounted to 43 g. (65%) m.p. 40°–45° C.

Step 4
-continued

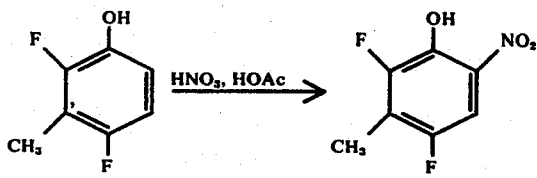

To a solution of 32 g (0.22 mole) of 2,4-difluoro m-cresol in 250 ml of glacial acetic acid at 0°–5° C was added dropwise with stirring a solution of 19.1 ml of concentrated nitric acid in 20 ml of glacial acetic acid. After one hour TLC (benzene-silica gel) showed no unreacted phenol. The mixture was poured into 500 ml of ice water and the yellow solid was filtered while cold. The weight of crude product was 34.5 g (83%). After crystallization from cyclohexane, the yellow crystals melted at 46°–48° C.

Step 5

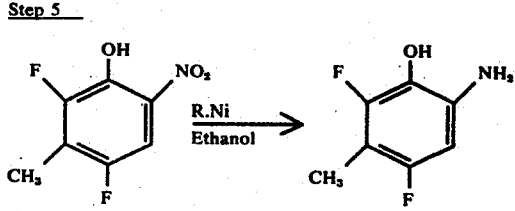

To a solution of 34.4 g (0.18 mole) of 2,4-difluoro-6-nitro m-cresol in 600 ml of absolute ethanol was added Raney nickel. The mixture was reduced at low pressure until there was no further uptake of hydrogen. The red solution was filtered and evaporated to low volume. Benzene (100 ml) was added and the solution was again evaporated to dryness. A yield of 28.5 g (98%) of crude amine was obtained, suitable for acylation without further purification.

Step 6

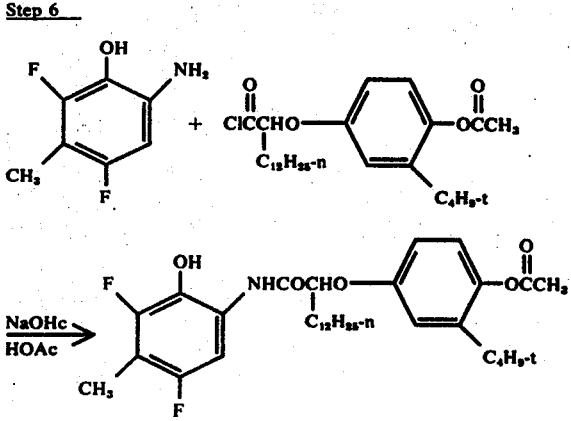

To a solution of 28.5 g (0.18 mole) of crude 6-amino-2,4-difluoro m-cresol in 1 liter of glacial acetic acid and 33.5 g of sodium acetate at 50° C. was added a solution of 81 g (0.18 mole) of alpha-[4-acetoxy-3-t-butyl-phenoxy]tetradecyl chloride in 150 ml of glacial acetic acid. After 30 minutes, TLC (1% $CH_3OH$ in $CHCl_3$ — silica gel) showed the reaction to be complete. The cooled solution was poured with vigorous stirring into 2 liters of ice water to give a milky suspension. Addition of a saturated sodium chloride solution produced a sticky gum which was dissolved in chloroform, dried over sodium sulfate and evaporated to low volume. The yield of crude product was 110 g. A sample recrystallized from acetonitrile showed m.p. 82°–84° C.

Step 7

6-[α-(3-t-butyl-4-hydroxyphenoxy)tetradecamido]2,4-difluoro-3-methylphenol

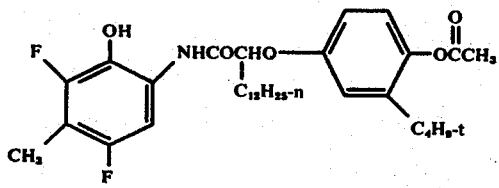

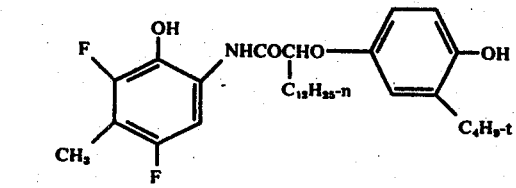

To a solution 110 g (0.19 mole) of the crude ester in 1 liter of methanol was added a solution of 11.45 g. (0.29 mole) of sodium hydroxide in 100 ml of methanol (1.5 equivalents). After 30 minutes stirring at room temperature, TLC (1% $CH_3OH$ in $CHCl_3$ — silica gel) showed no unreacted starting material. The mixture was poured with stirring into 2 liters of ice water, a saturated salt solution was added and a heavy gum separated. The gum was separated from the aqueous phase, dissolved in $CHCl_3$ dried over sodium sulfate and evaporated to a heavy oil which crystallized upon standing. The product was triturated with cyclohexane, filtered and recrystallized from acetonitrile to give 60 g (59%) of product which melted at 84°–85° C, solidified and remelted at 101°–102° C.

Note that in step 6, selection of the appropriate acyl halide (to be reacted with the 1-amino-2,4-difluorotoluol compound) will lead to any of a number of the coupler compounds of this invention specifically set out herein.

The invention has been described in detail with particular reference to preferred embodiments thereof, but, it will be understood that variations and modifications can be effected within the spirit and scope of the invention.

What is claimed is:

1. In a light-sensitive silver halide emulsion comprising at least one hydrophilic colloid, silver halide and a phenolic color-forming coupler compound capable of forming a cyan dye upon reaction with oxidized aromatic amino color developing agent;

the improvement wherein said phenolic color-forming coupler is a compound having the structure:

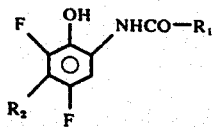

wherein R₁ is a ballasting group of the type useful in incorporated color-forming couplers and R₂ is lower alkyl or H.

2. In a photographic element comprising a support and at least one light-sensitive silver halide hydrophilic colloid emulsion layer containing, incorporated therein, a phenolic coupler compound capable of forming a cyan dye upon reaction with oxidized aromatic amino color developing agent;
the improvement wherein said
phenolic coupler is a compound having the structure:

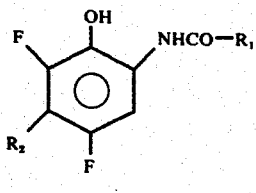

wherein R₁ is a non-interfering alkyl, aryl, substituted alkyl or substituted aryl coupler ballasting group of the type useful in photographic incorporated color-forming couplers, and R₂ is a lower alkyl or H.

3. An improved photographic element as in claim 2, wherein said phenolic coupler has the structure:

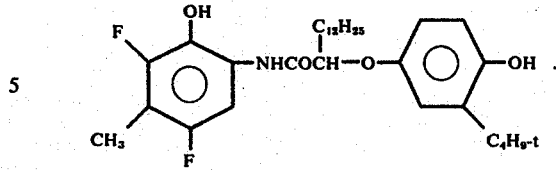

4. An improved photographic element as in claim 2, wherein said phenolic coupler has the structure:

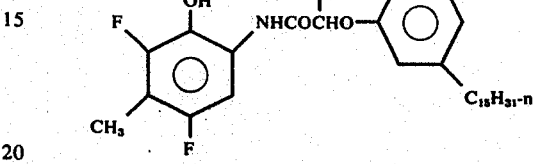

5. An improved photographic element as in claim 2, wherein said phenolic coupler has the structure:

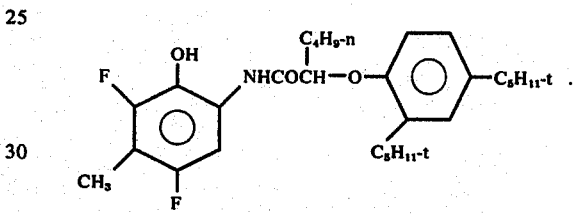

6. An improved photographic elememnt as in claim 2, wherein said phenolic coupler has the structure:

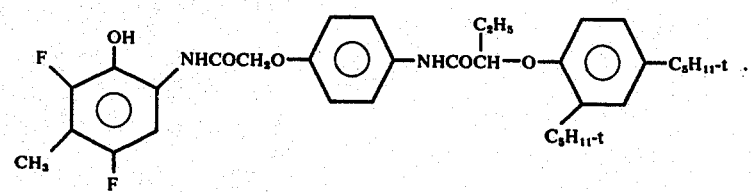

7. An improved photographic element as in claim 2, wherein said phenolic coupler has the structure:

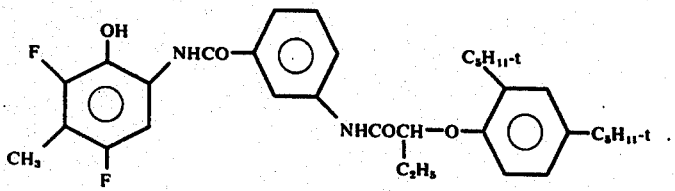

* * * * *

UNITED STATES PATENT AND TRADEMARK OFFICE
CERTIFICATE OF CORRECTION

PATENT NO. : 3,998,642
DATED : December 21, 1976
INVENTOR(S) : Philip T. S. Lau, Roy L. Orvis & Thomas E. Gompf It is certified that error appears in the above-identified patent and that said Letters Patent are hereby corrected as shown below:

Column 4, line 60, after "without" and before "yellow", insert ---a---;

Column 7, line 38, delete "01615";

Column 9, line 27, insert ---*Heat fade measured on densest portion--- and

Column 13, line 13, delete "*Heat fade measured on densest portion".

Signed and Sealed this

Tenth Day of May 1977

[SEAL]

Attest:

RUTH C. MASON
*Attesting Officer*

C. MARSHALL DANN
*Commissioner of Patents and Trademarks*